(12) United States Patent
Sasikumar et al.

(10) Patent No.: US 7,498,441 B2
(45) Date of Patent: Mar. 3, 2009

(54) BIARYLTETRAHYDROISOQUINOLINE PIPERIDINES AS SELECTIVE MCH RECEPTOR ANTAGONISTS FOR THE TREATMENT OF OBESITY AND RELATED DISORDERS

(75) Inventors: Thavalakulamgara K. Sasikumar, Edison, NJ (US); Wen-Lian Wu, Edison, NJ (US); Duane A. Burnett, Bernardsville, NJ (US); Li Qiang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 493 days.

(21) Appl. No.: 10/788,109

(22) Filed: Feb. 26, 2004

(65) Prior Publication Data
US 2004/0176355 A1 Sep. 9, 2004

Related U.S. Application Data

(60) Provisional application No. 60/450,799, filed on Feb. 28, 2003.

(51) Int. Cl.
C07D 217/00 (2006.01)
A61K 31/47 (2006.01)
(52) U.S. Cl. .................... 546/146; 514/307
(58) Field of Classification Search ............ 546/112, 546/114, 146; 514/279, 299, 307, 379
See application file for complete search history.

(56) References Cited

U.S. PATENT DOCUMENTS 5,908,830 A 6/1999 Smith et al.
6,964,972 B2 * 11/2005 Peters et al. ............... 514/304

FOREIGN PATENT DOCUMENTS

WO WO 02/06245 A 1/2002

WO WO 02/083134 A 10/2002

OTHER PUBLICATIONS

Hcaplus 77:164413, "Potential amebicides. VIII. Synthesis of 1-(Beta-arylethyl)-4-(omega-arylethylamino)alkyl-and 4-(1-tetrahydroisoquinolyl)alkylpipideridines", Jain et. al., Indian Journal of Chemistry (1972), 10 (5), 455-60.*
West, Anthony R., "Solid State Chemistry and its Applications", Wiley, New York, 1988, pp. 358 & 365.*
F. Zaragoza Dörwald "Side Reactions in Organic Synthesis: A Guide to Successful Synthesis Design" 2005 Wiley-VCH Verlag GmbH & Co. KGaA, Weinheim.*
Shimada et al., Nature, vol. 396 (Dec. 17, 1998), pp. 670-674.
International Search Report for PCT/US2004/005780—4 Pages.

* cited by examiner

*Primary Examiner*—Janet L Andres
*Assistant Examiner*—John Mabry
(74) *Attorney, Agent, or Firm*—Palaiyur S. Kalyanaraman; William Y. Lee

(57) ABSTRACT

The present invention discloses compounds which are novel antagonists for melanin-concentrating hormone (MCH), as well as methods for preparing such compounds. In other aspects, the invention is directed to pharmaceutical compositions comprising such MCH antagonists as well as methods of using them to treat obesity, metabolic disorders, eating disorders such as hyperphagia, and diabetes. Compounds of the invention generally have the structure:

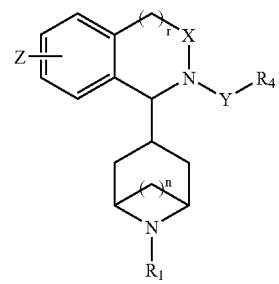

where the substituents are as defined herein.

19 Claims, No Drawings

BIARYLTETRAHYDROISOQUINOLINE PIPERIDINES AS SELECTIVE MCH RECEPTOR ANTAGONISTS FOR THE TREATMENT OF OBESITY AND RELATED DISORDERS

CROSS REFERENCE TO RELATED APPLICATIONS

This application claims the benefit of U.S. Provisional Application No. 60/450,799 filed on Feb. 28, 2003.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., Nature, Vol. 396 (17 Dec. 1998), pp. 670-673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist.

SUMMARY OF THE INVENTION

In one embodiment, this invention provides novel compounds having MCH antagonist activity. These compounds are represented by structural Formula 1:

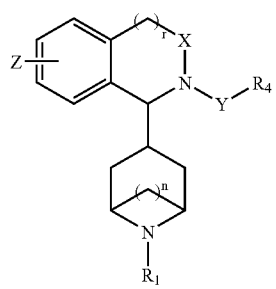

Formula 1 or a pharmaceutically acceptable salt or solvate of said compound, isomer or racemic mixture wherein X is $-CH_2-$, $-S(O_2)-$, carbonyl, $-CHCH_3$ or $-C(CH_3)_2-$;

Y is $-(CR^2R^3)_p-$, $-(CR^2R^3)_pC(O)NH-$, $-(CR^2R^3)_pNH-$, $-C(O)NH-$, $-C(O)(CR^2R^3)_pNH-$ or $-C(O)(CR^2R^3)_p-$;

Z is aryl, heteroaryl, $R^6$-substituted aryl or $R^6$-substituted heteroaryl;

n is 0, 2 or 3, and when n is 0, no connecting bond exists between the two carbons adjacent to the nitrogen;

p is 1, 2 or 3;

q is 1, 2, 3, 4, 5 or 6;

r is 0 or 1 and when r is 0, X is directly linked to the aromatic ring;

$R^1$ is hydrogen, -acyl, -alkyl, -cycloalkyl, -alkyl substituted with cycloalkyl, aralkyl, heteroaralkyl, $-C(O)R^5$, $-C(O)OR^5$, $-C(O)OR^8$, $-C(O)NR^8R^9$, $-S(O_2)R^5$, $-S(O_2)NR^8R^9$, cycloalkylalkyl, cycloalkylalkyl substituted with $R^{10}$ on the -cycloalkyl ring, heterocyclyl, aryl, heteroaryl or $-CF_3$;

$R^2$ and $R^3$ can be the same or different, each being independently hydrogen, alkoxy or alkyl; or $R^2$ and $R^3$ can be joined together and with the carbon to which they are attached to form a 3 to 7 membered ring;

$R^4$ is aryl, heteroaryl, $R^7$-substituted aryl or $R^7$ substituted heteroaryl or $Y-R^4$ taken together is

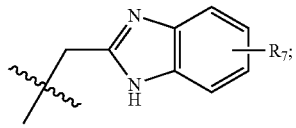

$R^5$ is alkyl, aryl, aralkyl, heteroaryl, cycloalkyl or heteroaralkyl;

$R^6$ is 1 to 5 substituents, each $R^6$ can be the same or different and each is independently selected from $-OH$, -alkoxy, $-OCF_3$, $-CN$, -alkyl, halogen, $-NR^8R^9$, $-CONR^8R^9$, $-NR^8S(O_2)R^6$, $-S(O_2)NR^8R^9$, $-S(O_2)R^5$, $-COR^5$, $-C(O)OR^8$, $-CF_3$, $-CHO$, $-C=NOR^8$,

$-(CR^8R^8)_qNC(O)R^{11}$, $-(CR^8R^8)_qNS(O_2)R^{12}$ and $-(CR^8R^8)_qNR^8R^9$ wherein the $R^8$ groups are independently selected;

$R^7$ is 1 to 5 substituents, each $R^7$ can be the same or different and each is independently selected from hydrogen, $-OH$, -alkoxy, $-OCF_3$, $-CN$, -alkyl, halogen, $-NR^8R^9$, $-CONR^8R^9$, $-NR^8S(O_2)R^6$, $-S(O_2)NR^8R^9$, $-S(O_2)R^5$, $-COR^5$, $-C(O)OR^8$, $-CF_3$, -alkyleneNR^8R^9$, $-CHO$, $-C=NOR^8$ and $-NR^8C(O)R^5$, or two adjacent $R^7$ groups can be joined together with two O atoms to form a methylene dioxy or ethylene dioxy group, $-(CR^8R^8)_qNR^8R^9$, $-(CR^8R^8)_qNC(O)R^{11}$ and $-(CR^8R^8)_qNS(O_2)R^{12}$, wherein the $R^8$ groups are independently selected;

$R^8$ is hydrogen or -alkyl;

$R^9$ is hydrogen, -alkyl, -aryl or -heteroaryl;

$R^{10}$ is $-OH$, -alkoxy, $-C(O)NR^8R^9$, $-NR^8R^9$, $-NR^8S(O_2)R^5$, $-NR^8C(O)NR^8R^9$, $-NR^8C(O)R^5$, $-NR^8C(O)OR^5$, $-C(O)OH$ or $-C(O)OR^5$;

$R^{11}$ is alkyl, aryl, alkoxy or $-NR^8R^9$; and $R^{12}$ is alkyl, aryl or $-NR^8R^9$.

Further wherein said aryl, heteroaryl, acyl, alkyl, cycloalkyl, heterocyclyl, aralkyl, heteroalkyl, heteroaralkyl, alkoxy and alkyene moieties can be unsubstitited or optionally independently substituted with one or more substituents as described herein.

This invention is also directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of Formula 1 or a pharmaceutically acceptable salt or solvate of said compound and a pharmaceutically acceptable carrier.

DETAILED DESCRIPTION OF THE INVENTION

In one embodiment, the present invention discloses MCH receptor antagonists represented by structural formula 1, or a pharmaceutically acceptable salt or solvate of said compound, isomer or racemic mixture thereof, wherein the various moieties are described above.

In a preferred embodiment of compounds of formula I, wherein X is —$CH_2$—, —$CHCH_3$ or —$C(CH_3)_2$—.

In another preferred embodiment, Y is —$(CR^2R^3)_pC(O)NH$—, —$C(O)NH$—, —$C(O)(CR^2R^3)_pNH$— or —$C(O)C(O)NH$—.

In another preferred embodiment, wherein Z is aryl, heteroaryl or $R^6$-substituted aryl.

In another preferred embodiment, wherein n is 0 and no connecting bond exists between the two carbons adjacent to the nitrogen.

In another preferred embodiment, wherein p is 1.

In another preferred embodiment, wherein q is 1, 2 or 3.

In another preferred embodiment, wherein r is 1.

In another preferred embodiment, wherein $R^1$ is hydrogen, -acyl, -alkyl, -cycloalkyl, -alkyl substituted with cycloalkyl, aralkyl, heteroaralkyl, —$C(O)R^5$, —$C(O)OR^8$, —$C(O)NR^8R^9$, —$S(O_2)R^5$, —$S(O_2)NR^8R^9$, cycloalkylalkyl substituted with $R^{10}$ on the -cycloalkyl ring, heterocyclyl, aryl or heteroaryl.

In another preferred embodiment, $R^2$ and $R^3$ can be the same or different, each being independently hydrogen, alkoxy or alkyl.

In another preferred embodiment, wherein $R^4$ is aryl, $R^7$-substituted aryl or $R^7$ substituted heteroaryl or Y—$R^4$ taken together is

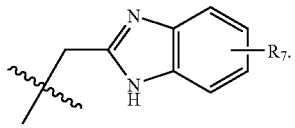

In another preferred embodiment, wherein $R^5$ is alkyl, aralkyl, cycloalkyl or heteroaralkyl.

In another preferred embodiment, wherein $R^6$ is 1 substituent and is independently selected from —OH, -alkoxy, —$OCF_3$, —CN, -alkyl, halogen, —$NR^8R^9$, —$CONR^8R^9$, —$NR^8S(O_2)R^6$, —$S(O_2)NR^8R^9$, —$S(O_2)R^5$, —$COR^5$, —$C(O)OR^8$, —$CF_3$, —CHO, —C=$NOR^8$,

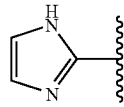

and —$(CR^8R^8)_qNR^8R^9$ wherein the $R^8$ groups are independently selected.

In another preferred embodiment, wherein $R^7$ is 1 or 2 substituents, each $R^7$ can be the same or different and each is independently selected from hydrogen, —OH, -alkoxy, —$OCF_3$, —CN, -alkyl, halogen, —$NR^8R^9$, —$CONR^8R^9$, —$NR^8S(O_2)R^6$, —$S(O_2)NR^8R^9$, —$S(O_2)R^5$, —$COR^5$, —$C(O)OR^8$, —$CF_3$, -alkyleneNR^8R^9, —CHO, —C=$NOR^8$ and —$NR^8C(O)R^5$, or two adjacent $R^7$ groups can be joined together to form a methylene dioxy or ethylene dioxy group, —$(CR^8R^8)_qNR^8R^9$, —$(CR^8R^8)_qNC(O)R^{11}$ and —$(CR^8R^8)_qNS(O_2)R^{12}$, wherein the $R^8$ groups are independently selected.

In another preferred embodiment, wherein $R^8$ is -alkyl.

In another preferred embodiment, wherein $R^9$ is hydrogen or -alkyl.

In another preferred embodiment, wherein $R^{10}$ is —OH, -alkoxy, —C(O)OH or —$C(O)OR^5$.

In another preferred embodiment, wherein $R^{11}$ is alkyl, aryl or alkoxy.

In another preferred embodiment, wherein $R^{12}$ is alkyl or aryl.

In additional preferred embodiments of the above Formula 1: Z is cyanophenyl or pyridinyl such as cyano-3-phenyl, pyridine-3-yl or pyridine-4-yl. Additional preferred embodiments include the embodiments represented by Formula 1 wherein $R^4$ is 3,5 dichlorophenyl. Compounds represented by Formula 1 wherein $R^1$ is -alkyl, -cycloalkyl, -aralkyl, -heteroaralkyl and -heterocyclyl are also preferred.

Still additional preferred embodiments of Formula 1 include compounds wherein: X is —$S(O_2)$— or X is —$CH_2$—.

In other preferred embodiments are the compounds of Formula 1, wherein Y is —$C(R^2R^3)C(O)NH$—. Still other preferred embodiments of the compounds of Formula 1 are wherein $R^2$ and $R^3$ are hydrogen, alkyl or alkoxy; n is 0; and r is 0; as well as compounds of Formula 1 wherein $R^2$ and $R^3$ are hydrogen.

Preferred embodiments further include embodiments that are represented by Formula 1 wherein X is carbonyl; Y is —$C(R^2R^3)C(O)NH$— and $R^2$ and $R^3$ are hydrogen but can, in the alternative, also be alkyl or alkoxy; n is 0 and r is 0.

Preferred compounds also include those wherein $R^1$ is hydrogen, -alkyl, -cycloalkyl, -alkyl substituted with -cycloalkyl, -alkyl substituted with $R^{10}$, —$S(O_2)R5$, —$C(O)R^5$ or —$C(O)OR^8$; $R^2$ and $R^3$ are hydrogen, alkyl or alkoxy; n is 0; r is 1; Z is aryl or $R^6$-substituted aryl and most preferably wherein $R^6$ represents a single substituent.

In many preferred cases, $R^4$ is 3,5 dichlorophenyl and $R^1$ is hydrogen, methyl, ethyl, hydroxyethyl, cyclopentyl, propyl, —$S(O_2)CH3$, —$C(O)CH_3$, —$C(O)OC(CH_3)_3$, isopropyl, cyclopropylmethyl, heteroaryl or

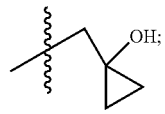

$R^2$ and $R^3$ are hydrogen; Z is $R^6$-substituted aryl; $R^6$ is 1 to 5 substituents and each is independently selected from the group consisting of halogen, —$CF_3$, —$OCF_3$, —CN, —CHO, —$S(O_2)R^5$, —$C(O)OR^8$, —$COR^5$, —$C(O)NR^8R^9$,

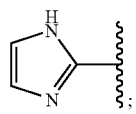

and $R^7$ is two substituents which can be the same or different and independently selected from halogen, —CN, —CF$_3$.

One class of preferred compounds is that in which Z is a monocyclic aryl group with a single $R^6$ substituent in the meta position relative to the point of attachment to the aromatic position show in Formula 1.

In another class of preferred compounds Z is a monocyclic aryl group and $R^6$ is —CN.

In still another class of preferred compounds wherein Z is a monocyclic aryl group, $R^6$ is —CN and $R^1$ is hydrogen, methyl, ethyl, hydroxyethyl, cyclopentyl, —S(O$_2$)CH3, —C(O)CH$_3$, isopropyl or cyclopropylmethyl.

Still yet another class of preferred compounds of Formula 1 has the structure:

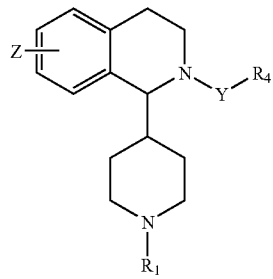

Formula 2 wherein
Y is —(CR$_2$R$_3$)$_p$C(O)NH—;
Z is phenyl,

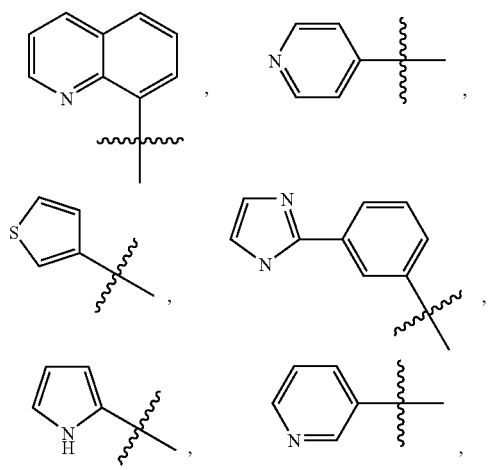

or any of the foregoing radicals substituted with a cyano, fluoro, chloro, methoxy, trifluoromethyl, trifluoromethoxy, formyl or a carboxyl group, or Z is a 2,5-dichlorophenyl group;

$R^1$ is cyclopentyl, methyl, benzyl, hydrogen, 5-hydroxy-n-pentyl, cycloheptyl, N-methylpiperidene-4-yl, 4-oxacyclohexyl, 3-thiacyclopentyl, furane-3-ylmethyl, 2-methoxybenzyl, cyclopropylmethyl, cyclobutyl, 3-phenylpropyl, isopropyl, cyclohexyl, cyclopentylcarbonyl, diethylaminocarbonyl, acetyl, methylsulfonyl, dimethylaminosulfonyl, thiazole-2-ylmethyl or ethylsulfonyl; and $R^4$ is aryl, heteroaryl, $R^7$-substituted aryl or $R^7$ substituted heteroaryl or Y—$R^4$ taken together is

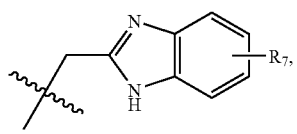

wherein $R^7$ is present or not and if present is independently hydrogen, chloro or fluoro.

Z is suitably selected from the following radicals:

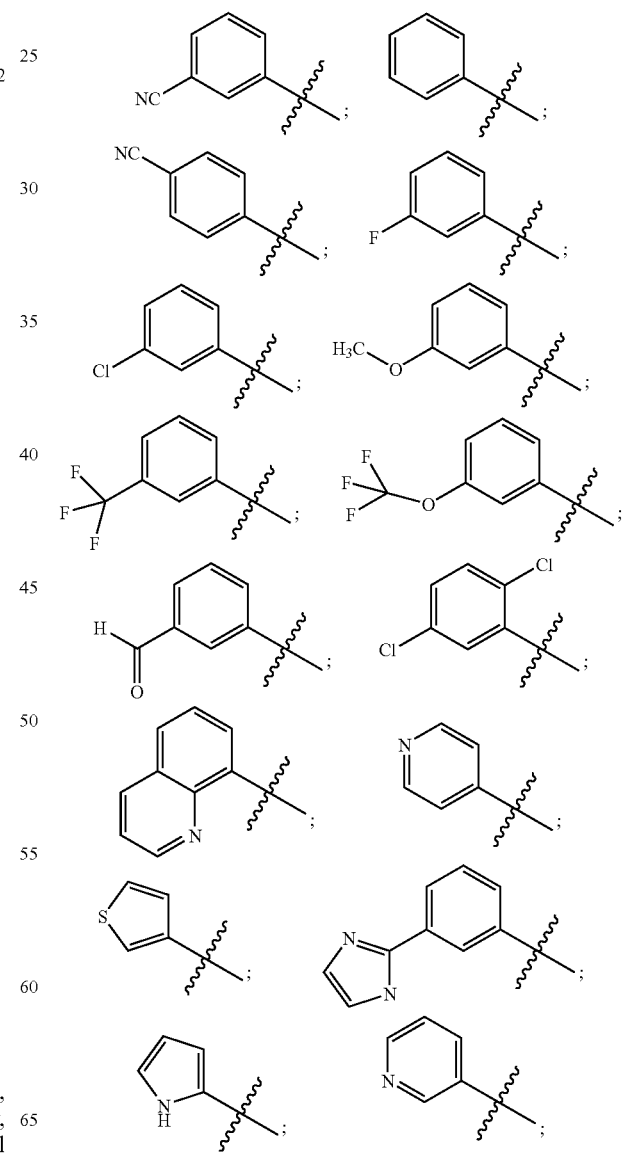

-continued
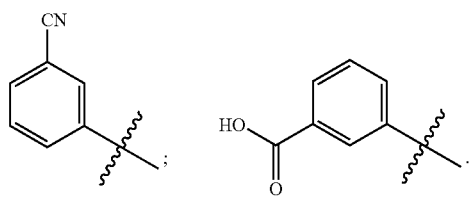
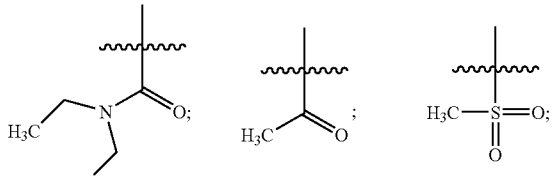
$R^1$ is suitably selected from the following radicals:
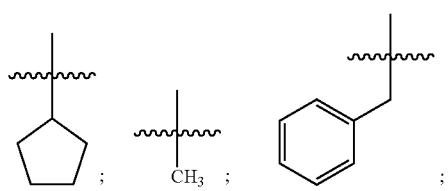
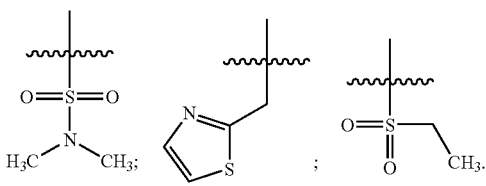
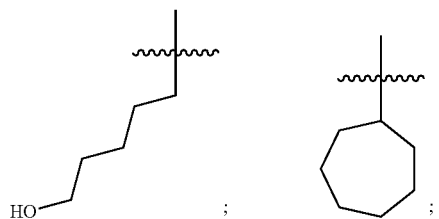
Preferred compounds of Formula 1 include but are not limited to:
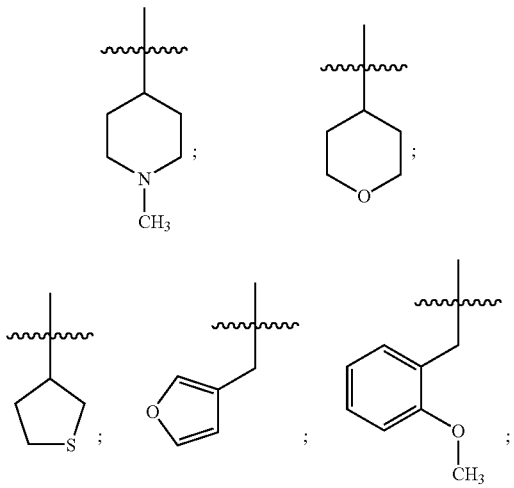
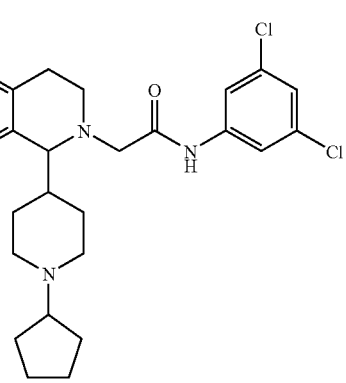
Ex. 1
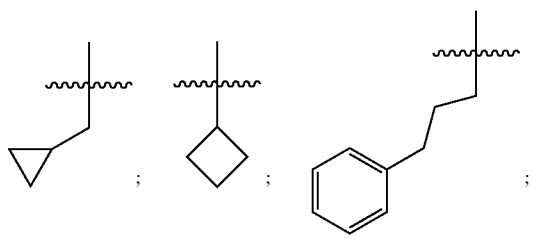
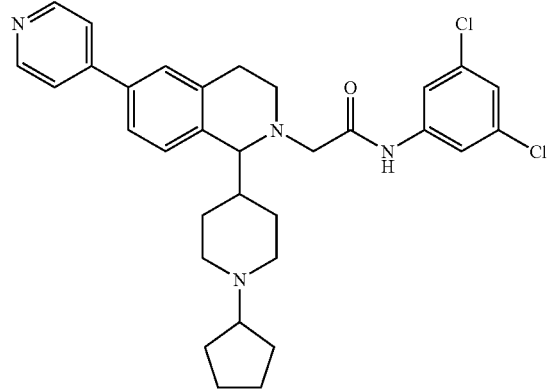
Ex. 12

-continued
Ex. 16
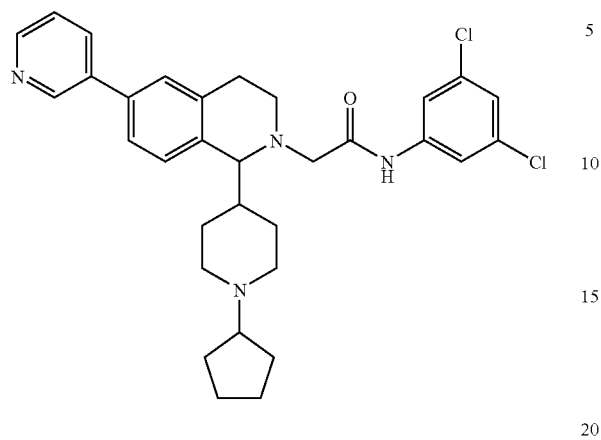
Ex. 17
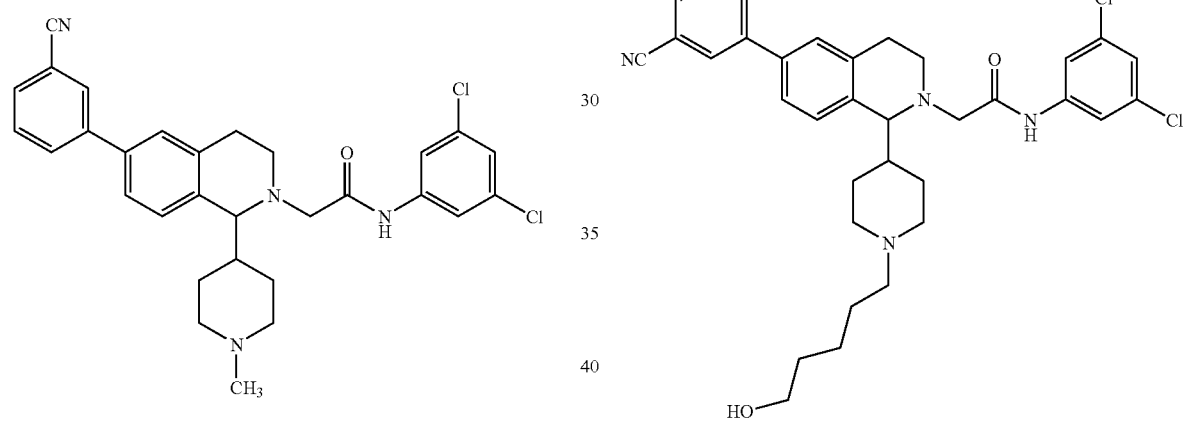
Ex. 19
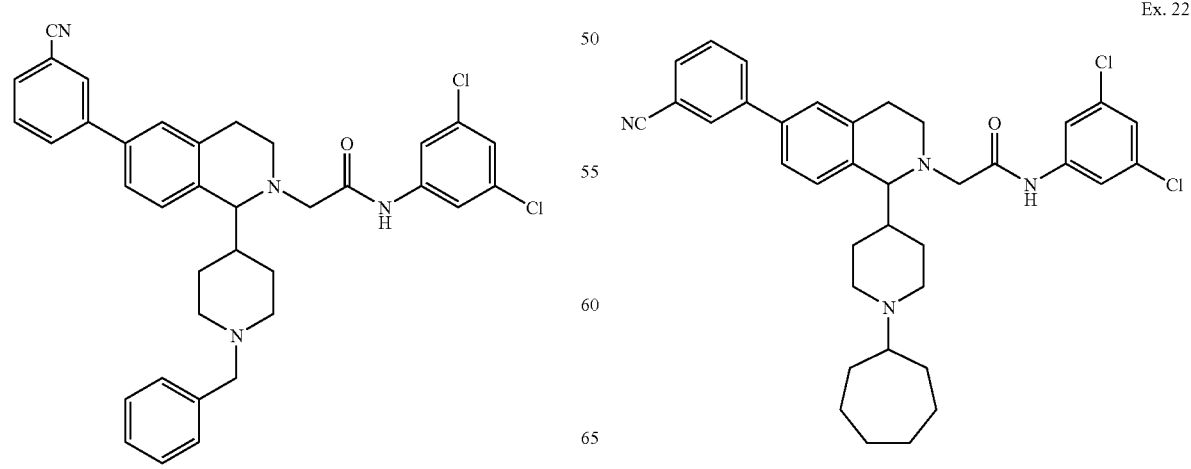
-continued
Ex. 20
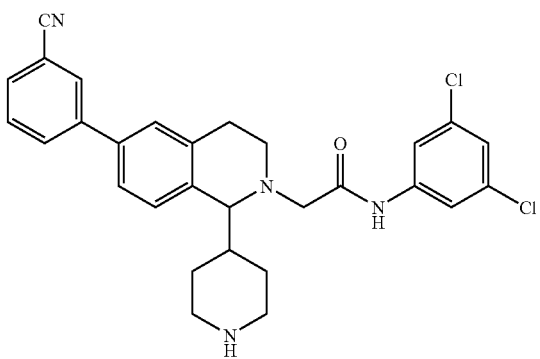
Ex. 21
Ex. 22

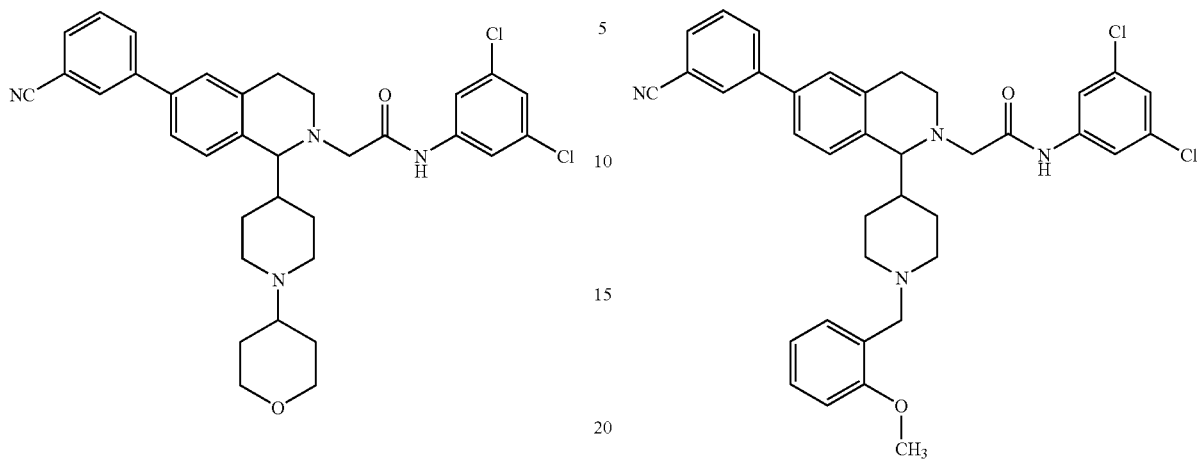
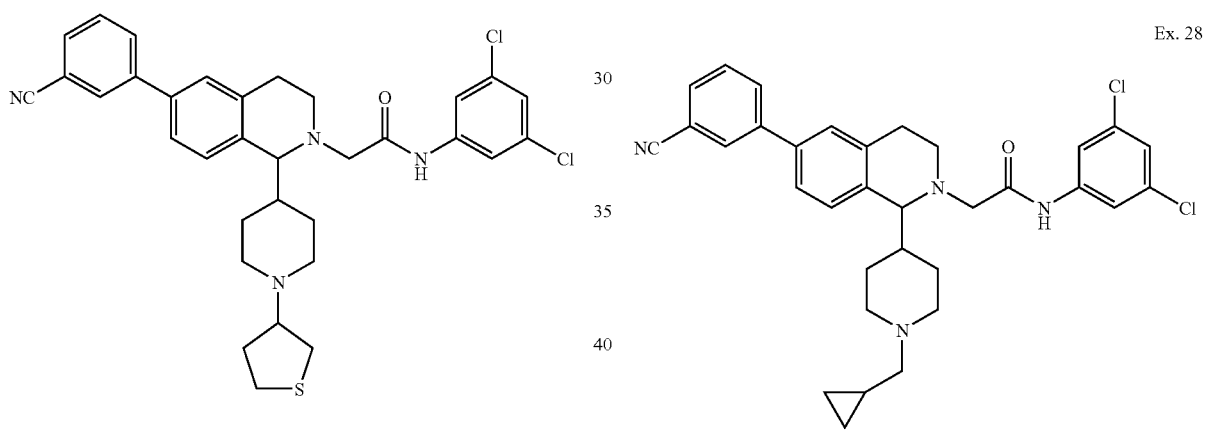
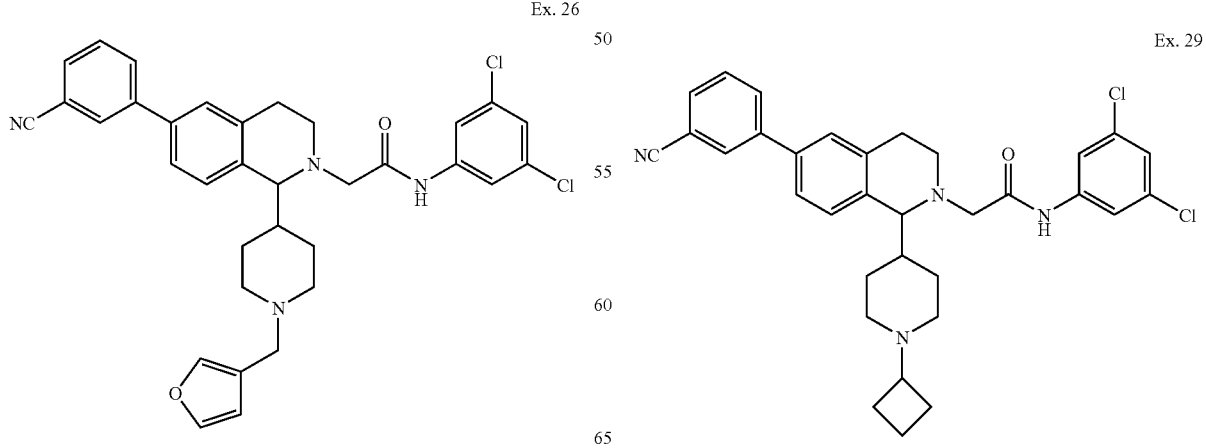

-continued

Ex. 32

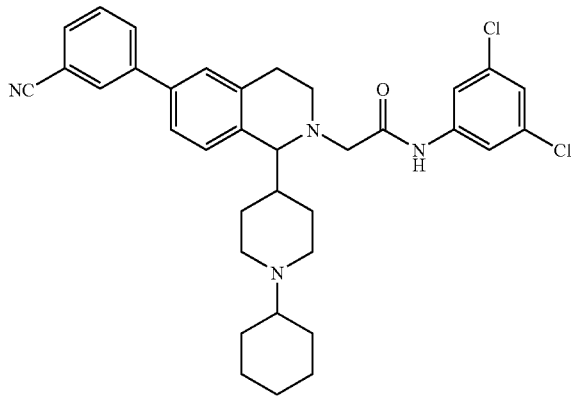

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Acyl" means an H—C(O)—, alkyl-C(O)—, alkenyl-C(O)—, alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, -cycloalkyl, cyano, and alkoxy. Non-limiting examples of suitable alkenyl groups include ethenyl, propenyl, n-butenyl, and 3-methylbut-2-enyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen. The term "substituted alkoxy" means that the alkyl portion of the alkoxy group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkoxycarbonyl" means an alkoxy group defined earlier linked to an adjacent moiety through a carbonyl. Non-limiting examples of alkoxycarbonyl groups include —C(O)—CH$_3$, —C(O)—CH$_2$CH$_3$ and the like.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkylaryl" means an alkyl-aryl- group in which the alkyl and aryl are as previously described. Preferred alkylaryls comprise a lower alkyl group. Non-limiting example of a suitable alkylaryl groups is tolyl. The bond to the parent moiety is through the aryl.

"Alkylene" means an alkanediyl group commonly having free valencies on two carbon atoms. Non-limiting examples include methylene, ethylene, propylene and the like. The term "substituted alkylene" means that the alkylene group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl.

"Alkylsulfinyl" means an alkyl-S(O)— group. Preferred groups are those in which the alkyl group is lower alkyl. The bond to the parent moiety is through the sulfinyl.

"Alkylsulfonyl" means an alkyl-S(O$_2$)— group. Preferred groups are those in which the alkyl group is lower alkyl. The bond to the parent moiety is through the sulfonyl.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl. The term "substituted alkynyl" means that the alkynyl group may be substituted by one or more substituents which may be the same or different, each substituent being independently selected from the group consisting of alkyl, aryl and -cycloalkyl.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from the group consisting of halo, alkyl, aryl, -cycloalkyl, cyano, hydroxy, alkoxy, alkylthio, amino, —NH (alkyl), —NH(cycloalkyl), —N(alkyl)$_2$, carboxy and —C(O)O-alkyl.

"Aralkylthio" means an aralkyl-S— group in which the aralkyl group is as previously described. Non-limiting example of a suitable aralkylthio group is benzylthio. The bond to the parent moiety is through the sulfur.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, —OCF$_3$, —OCOalkyl, —OCOaryl, —CF$_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl. heteroarylsulfonyl, alkylsulfinyl, arylsulfinyl, heteroarylsulfinyl, alkylthio, arylthio, heteroarylthio, aralkylthio, heteroaralkylthio, -cycloalkyl and heterocyclyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Aryloxy" means an aryl-O— group in which the aryl group is as previously described. Non-limiting examples of suitable aryloxy groups include phenoxy and naphthoxy. The bond to the parent moiety is through the ether oxygen.

"Arylsulfinyl" means an aryl-S(O)— group. The bond to the parent moiety is through the sulfinyl.

"Arylsulfonyl" means an aryl-S(O$_2$)— group. The bond to the parent moiety is through the sulfonyl.

"Arylthio" means an aryl-S— group in which the aryl group is as previously described. Non-limiting examples of suitable arylthio groups include phenylthio and naphthylthio. The bond to the parent moiety is through the sulfur.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Halogen" means fluorine, chlorine, bromine or iodine. Preferred are fluorine, chlorine or bromine, and more preferred are fluorine and chlorine.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Cycloalkylalkyl" means a cycloalkyl-alkyl group in which the cycloalkyl and alkyl are as previously described. Preferred cycloalkylalkyls contain a lower alkyl group. A non limiting example includes cyclopropylmethyl. The bond to the parent moiety is through the alkyl. The "cycloalkylalkyl" can be optionally substituted on the ring by one or more substitutents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl. The "heteroaralkyl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring or hydrogen(s) on any nitrogen(s) suitably by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Mammal" means humans and other mammalian animals.

"Patient" includes both human and other animals.

The term "optionally substituted" means optional substitution with the specified groups, radicals or moieties. It should also be noted that any heteroatom with unsatisfied valences in the text, schemes, examples, structural formulae, and Tables herein is assumed to have the hydrogen atom or atoms to satisfy the valences.

When any variable (e.g., aryl, heterocycle, $R^2$, etc.) occurs more than one time in any constituent or in Formula 1, its definition on each occurrence is independent of its definition at every other occurrence. Also, combinations of substituents and/or variables are permissible only if such combinations result in stable compounds.

The compounds of Formula 1 can be administered as racemic mixtures or enantiomerically pure compounds.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective to treat a mammal (e.g., human) having a disease or condition mediated by MCH, and thus producing the desired therapeutic effect.

Prodrugs and solvates of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The compounds of formula I can form salts, solvates and prodrugs which are also within the scope of this invention. Reference to a compound of formula I herein is understood to include reference to salts, solvates and prodrugs thereof, unless otherwise indicated.

The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the Formula 1 may be formed, for example, by reacting a compound of Formula 1 with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula 1, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

Compounds of Formula 1 can be highly selective, high affinity Melanin Concentrating Hormone (MCH) receptor antagonists useful for the treatment of obesity.

Another aspect of this invention is a method of treating a mammal (e.g., human) having a disease or condition mediated by MCH by administering a therapeutically effective amount of at least one compound of Formula 1, or a pharmaceutically acceptable salt or solvate of said compound to the mammal.

A preferred dosage is about 0.001 to 100 mg/kg of body weight/day of the compound of Formula 1. An especially preferred dosage is about 0.01 to 30 mg/kg of body weight/day of a compound of Formula 1, or a pharmaceutically acceptable salt or solvate of said compound.

Still yet another aspect of this invention is directed to a method of treating obesity comprising administering to a mammal in need of such treatment a therapeutically effective amount of at least one compound of Formula 1, or a pharmaceutically acceptable salt or solvate of said compound.

A further aspect of this invention is directed to a method for treating eating and metabolic disorders such as bulimia and anorexia comprising administering to a mammal a therapeutically effective amount of at least one compound of Formula 1, or a pharmaceutically acceptable salt or solvate of said compound.

A still yet further aspect of this invention is directed to a method for treating hyperlipidemia comprising administering to a mammal a therapeutically effective amount of at least one compound of Formula 1 or a pharmaceutically acceptable salt or solvate of said compound.

Another further aspect of this invention is directed to a method for treating cellulite and fat accumulation comprising administering to a mammal a therapeutically effective amount of at least one compound of Formula 1, or a pharmaceutically acceptable salt or solvate of said compound.

Another aspect of this invention is directed to a method for treating type II diabetes comprising administering to a mammal a therapeutically effective amount of at least one compound of Formula 1 or a pharmaceutically acceptable salt or solvate of said compound.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula 1, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula 1, or a pharmaceutically acceptable salt or solvate of said compound and at least one pharmaceutically acceptable carrier.

Still yet other aspects of this invention are combinations of a compound of Formula 1, or a pharmaceutically acceptable salt or solvate of said compound and other compounds as described below.

Accordingly, included within the invention is a method for treating obesity comprising administering to a mammal (e.g., a female or male human)

a. an amount of a first compound, said first compound being a compound of Formula 1, or a pharmaceutically acceptable salt or solvate of said compound; and b. an amount of a second compound, said second compound being an antiobesity and/or anorectic agent such as a $\beta_3$ agonist, a thyromimetic agent, an anoretic agent, or an NPY antagonist and/or optionally a pharmaceutically carrier, vehicle or diluent, wherein the amounts of the first and second compounds result in a therapeutic effect.

Another aspect of this invention is a kit comprising:

a. an amount of a compound of Formula 1, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of Formula 1, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or N-(2-Benzoylphenyl)-O-[2-(methyl-2-pyridinylamino)ethyl]-L-tyrosine, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of Formula 1, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or N-(2-Benzoylphenyl)-O-[2-(methyl-2-pyridinylamino) ethyl]-L-tyrosine, a sulfonylurea, glipazide, glyburide, or clorpropamide; and optionally a pharmaceutical carrier, vehicle or diluent.

Another aspect of this invention is a kit comprising:

a. an amount of a compound of Formula 1, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or N-(2-Benzoylphenyl)-O-[2-(methyl-2-pyridinylamino)ethyl]-L-tyrosine, a sulfonylurea, glipazide, glyburide, or chlorpropamide arid a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Compounds of Formula 1 can be produced by processes known to those skilled in the art using either solution phase or solid phase synthesis as shown in the following reaction schemes, in the preparations and examples below.

SYNTHESIS

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% $CH_3CN$, 5 min-95% $CH_3CN$, 7 min-95% $CH_3CN$, 7.5 min-10% $CH_3CN$, 9 min-stop. The observed parent ion using electro spray ionization are given.

The following abbreviations are utilized throughout the experimental procedures described below:

$BBr_3$ means tribromo borane;

$BrCH_2CONHAr$ means 3,5-dichlorophenyl bromoacetamide;

$CH_3CN$ means acetonitrile;

ES MS means electro spray mass spectrometry $K_2CO_3$ means potassium carbonate;

MeOH means methanol;

$PhNTF_2$ means N-phenyltrifluoromethane sulfonimide;

$SiO_2$ means silicon dioxide;

TFA means trifluoroacetic acid;

Alternative mechanistic pathways and analogous structures within the scope of the invention would be apparent to those skilled in the art.

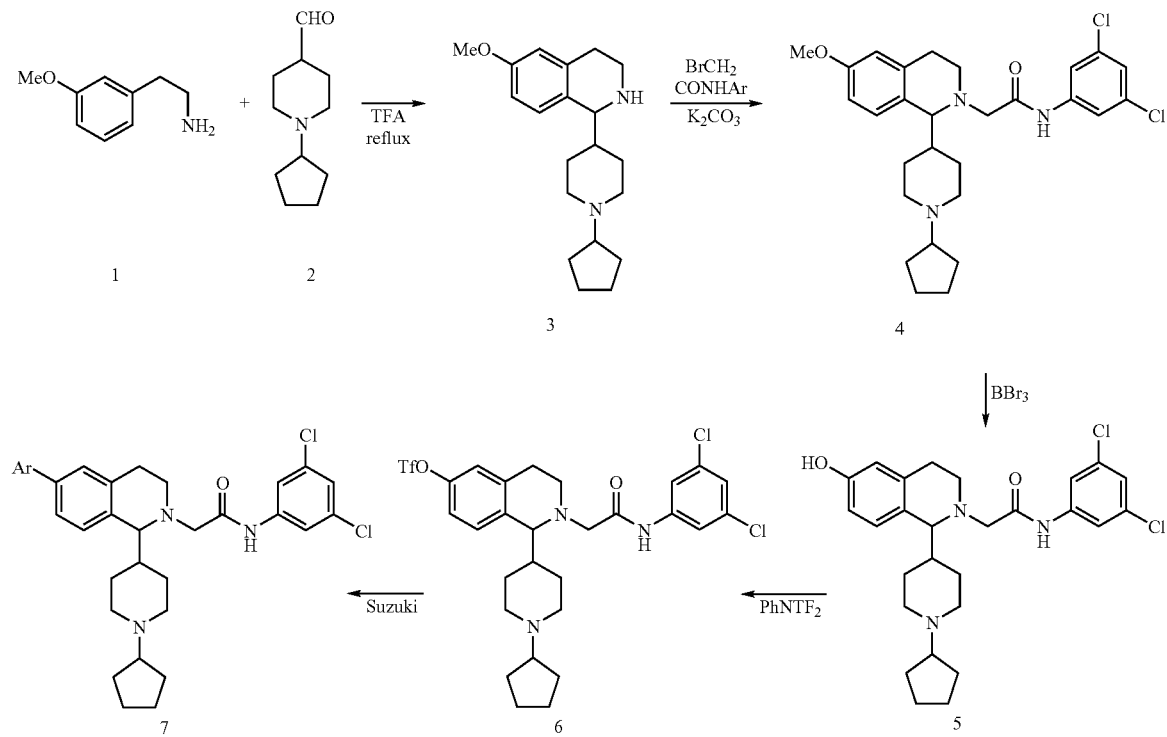

Scheme 1

Experimental Procedure:

Compound 3: To a mixture of 3-methoxyphenethylamine (0.9 g, 5.5 mmol) and N-cyclopentyl piperidine carboxaldehyde (1.0 g, 5.5 mol, 1 eq) at 0° C. was added triflouroacetic acid (5 mL) and the resulting mixture was stirred at room temperature for 1 h and the contents were heated at 100° C. for 4 h. The reaction mixture was poured into crushed ice and extracted with dichloromethane (2×200 mL). The combined organic layers were washed with sodium bicarbonate solution and dried over sodium sulfate. The solvent was removed in vacuo and the product was isolated by silica gel column chromatography eluting with 5% methanol/dichloromethane as eluent to give 0.65 g of product (3) as oil: ES MS: calcd for $C_{20}H_{31}N_2O^+$=315.47; found=315.1 (M+1)$^+$ Compound 4: Compound 3 (0.65 g, 2.0 mmol) was dissolved in 10 mL of acetonitrile and treated with 0.65 g (1.15 eq) of 2-bromo-N-(3,5-dichlorophenyl)-acetamide and 1.0 g (3.6 eq) of $K_2CO_3$. The reaction was heated in a sealed tube at 60° C. for 3 hours. The solvent was removed in vacuo and the product was isolated by SiO$_2$ column eluting with 5% methanol/dichloromethane as eluent to give 0.7 g of 4 as oil. ES MS: calcd for $C_{28}H_{37}Cl_2N_3O_2^+$=516.5; found=516.1 (M+1)$^+$ Compound 5: To a solution of compound 4 (0.642 g, 1.24 mmol) in 50 mL of dichloromethane at −78° C. was added 0.35 mL of BBr$_3$ (3.0 eq) and the reaction was stirred at that temperature for 30 minutes. The reaction mixture was warmed to room temperature and stirred for 2 h. Additional 0.12 mL of BBr$_3$ was added at room temperture and stirred for another 3 h. The reaction mixture was cooled to −78° C. and quenched with 20 mL of MeOH and warmed to room temperature. The mixture was then heated under reflux for 30 minutes. The solvent was removed in vacuo and the product was isolated by SiO$_2$ chromatography eluting with 10% methanol/dichloromethane as eluent to give 0.4 g of compound 5 as a light brown solid. ES MS: calcd for $C_{27}H_{34}Cl_2N_3O_2^+$=502.48; found=502.1 (M+1)$^+$ Compound 6: The phenol (0.4 g, 0.79 mmol) was dissolved in 100 mL of dichloromethane and 5 mL of triethylamine was added to get a clear solution. This solution was cooled to −78° C. and treated with N-phenyl trifluoromethane sulfonimide (2.0 g, 5.5 mmol) and stirred for 1 h. The reaction mixture was warmed to room temperature and stirred for 4 hours. 100 mL of water was added to the reaction mixture. The mixture was extracted with ethyl acetate and the organic layer was washed sequentially with sodium bicarbonate solution and brine. It was dried over sodium sulfate and the solvent was removed in vacuo. The resulting triflate was isolated by a short SiO$_2$ column eluting with 80% ethylacetate/hexane as eluent. ES MS: calcd for $C_{28}H_{33}Cl_2F_3N_3O_4S^+$=634.54; found=634.1 (M+1)$^+$ Compound 7: The triflate 6 (0.1 g, 0.157 mmol) was dissolved in 20 mL of toluene/methanol (1:1) and treated with 3-cyanophenyl boronic acid (0.05 g, 0.34 mol, 2 eq) and sodium carbonate solution (2M aq. solution, 1 mL). The reaction mixture was degassed with nitrogen for 2 minutes and treated with tetrakistriphenylphosphine palladium (0.05 g, 12 mol %). The reaction was heated at 90° C. for 4 h. The solid particles were filtered off through a small pad of celite and washed with ethyl acetate. The solvent was removed in vacuo and the product was isolated by SiO$_2$ chromatography eluting with 5% methanol/dichloromethane as eluent to get 0.04 g of product 7. ES MS: calcd for $C_{34}H_{37}Cl_2N_4O^+$=587.58; found =587.1 (M+1)$^+$ Compound 11 was synthesized using analogous chemical transformations. The removal of benzyl group was achieved with chloroethylchloroformate reaction.

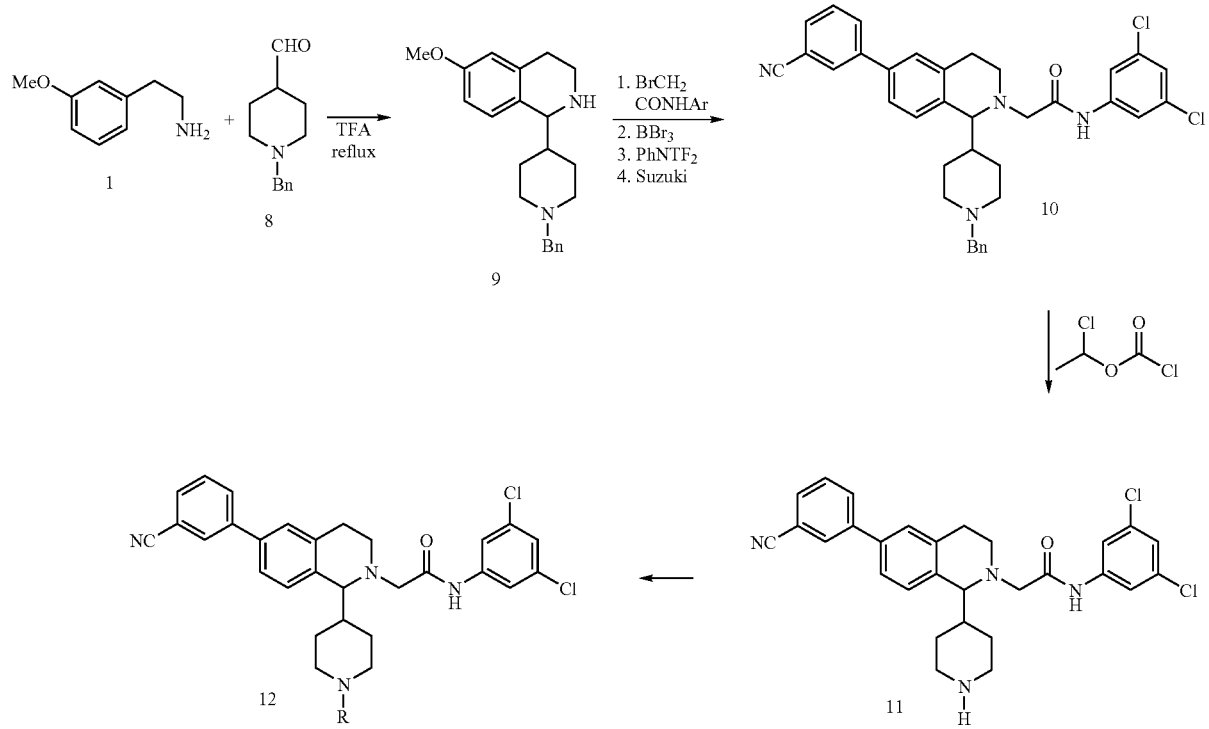

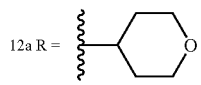

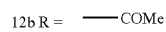

Compound 11: To a solution of compound 10 (0.73 g, 1.2 mmol) in dichloroethane (15 mL) was added chloroethyl chloroformate (0.39 mL, 3 eq) at 0° C. and the mixture was heated under reflux for 1.5 hours. The solvent was removed in vacuo and the residue was redissolved in MeOH (20 mL) and heated under reflux for 1 h. The solvent was removed in vacuo and the product was isolated by $SiO_2$ chromatography eluting with 4-5% methanol/dichloromethane as eluent to get 0.047 g of product 11. ES MS: calcd for $C_{29}H_{29}Cl_2N_4O^+$=519.46; found=519.1 $(M+1)^+$ General Procedure for Reductive Alkylation, Sulfonylation and Acylation:

1. Reductive Alkylation

The secondary amine 11 (0.010 g, 0.019 mmol) was dissolved in dichloro-methane (anhydrous, 1 ml), treated with sodium triacetoxyborohydride (0.057 mmol, 3 eq) and aldehyde/ketone (0.19 mmol, 10 eq), left for stirring over night at room temperature. The reaction mixture was then treated with Amberlyst-15 ion-exchange resin (Aldrich, 0.01 g, 20 eq) for 2 h. The resin was washed with dichloromethane, tetrahydrofuran and methanol for 3 times. The resin was then treated with ammonia in methanol (2N, 2 ml) for 15 minutes (2 times). The resin was removed by filtration. All the solvent was removed in vacuo to give the desired product.

2. Sulfonylation, Acylation

The secondary amine 11 (0.010 g, 0.019 mmol) was dissolved in dichloromethane (anhydrous, 1 ml), treated with resin-bound DIEA (Argonaut, 0.006 g, 10 eq) and acetyl chloride/sulfonyl chloride (0.19 mmol, 10 eq), left for stirring over night at room temperature. The reaction mixture was then treated with resin-bound isocyanate (Argonaut, 0.002 g, 12 eq) for 2 h. The resin was removed by filtration. All the solvent was removed in vacuo to give the desired product.

Compound 12a: Compound 11 (0.010 g, 0.019 mmol) was dissolved in dichloromethane (anhydrous, 1 ml), treated with sodium triacetoxyborohydride (0.057 mmol, 3 eq) and tetrahydro-pyran-4-one (0.19 mmol, 10 eq), left for stirring over night at room temperature. The reaction mixture was then treated with Amberlyst-15 ion-exchange resin (Aldrich, 0.01 g, 20 eq) for 2 h. The resin was washed with dichloromethane, tetrahydrofuran and methanol for 3 times. The resin was then treated with ammonia in methanol (2N, 2 ml) for 15 minutes (2 times). The resin was removed by filtration. All the solvent was removed in vacuo to get 0.0085 g of product 12a. ES MS: calcd for $C_{34}H_{37}Cl_2N_4O_2^+$=603.58; found=603.1 $(M+1)^+$ Compound 12b: Compound 11 (0.010 g, 0.019 mmol) was dissolved in dichloromethane (anhydrous, 1 ml), treated with resin-bound DIEA (Argonaut, 0.006 g, 10 eq) and acetyl chloride (0.19 mmol, 10 eq), left for stirring over night at room temperature. The reaction mixture was then treated with resin-bound isocyanate (Argonaut, 0.002 g, 12 eq) for 2 h. The resin was removed by filtration. All the solvent was removed in vacuo to get 0.0122 g of product (12b). ES MS: calcd for $C_{31}H_{31}Cl_2N_4O_2^+$=561.5; found=561.1 $(M+1)^+$ Compound 12c: Compound 11 (0.010 g, 0.019 mmol) was dissolved in dichloromethane (anhydrous, 1 ml), treated with resin-bound DIEA (Argonaut, 0.006 g, 10 eq) and methane sulfonyl chloride (0.19 mmol, 10 eq), left for stirring over night at room temperature. The reaction mixture was then treated with resin-bound isocyanate (Argonaut, 0.002 g, 12 eq) for 2 h. The resin was removed by filtration. All the solvent was removed in vacuo to get 0.0069 g of product 12c. ES MS: calcd for $C_{30}H_{31}Cl_2N_4O_3S^+$=597.56; found=597.1 $(M+1)^+$ MCH Receptor Binding Assay:

Membranes from CHO cells expressing the MCH receptor were prepared by lysing cells with 5 mM HEPES for 15 min at 4 C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4× the desired final concentration). Nonspecific binding was determined by including 1 μM MCH in the binding reaction. The binding reaction was incubated at room temperature for 2 h. Plates were then analyzed in a TOP-COUNT microplate scintillation counter (Packard). Data was analyzed and Ki values for the compounds of Formula 1 were determined using GraphPad Prim.

Following the above procedures, compounds of Formula 1 having the structure shown in Table 1 were prepared.

TABLE 1

Examples 1-45

| EX | MOLSTRUCTURE | MOL FORMULA | MOL WGT | Obsd m/z |
|----|---|---|---|---|
| 1 | | $C_{34}H_{36}Cl_2N_4O$ | 587.598 | 587.1 |
| 2 | | $C_{33}H_{37}Cl_2N_3O$ | 562.588 | 562.1 |
| 3 | | $C_{34}H_{37}Cl_2N_4O$ | 587.598 | 587.1 |

TABLE 1-continued

Examples 1-45

| EX | MOLSTRUCTURE | MOL FORMULA | MOL WGT | Obsd m/z |
|---|---|---|---|---|
| 4 | | $C_{33}H_{36}Cl_2FN_3O$ | 580.579 | 580.1 |
| 5 | | $C_{33}H_{36}Cl_3N_3O$ | 597.033 | 597.1 |
| 6 | | $C_{34}H_{39}Cl_2N_3O_2$ | 592.615 | 592.1 |

TABLE 1-continued
Examples 1-45
| EX | MOLSTRUCTURE | MOL FORMULA | MOL WGT | Obsd m/z |
|---|---|---|---|---|
| 7 | 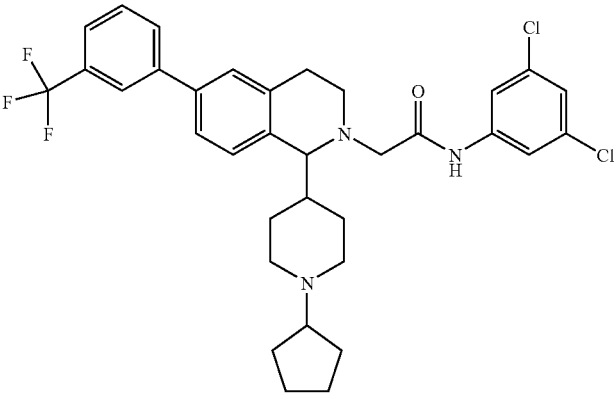 | $C_{34}H_{36}Cl_2F_3N_3O$ | 630.587 | 630.1 |
| 8 | 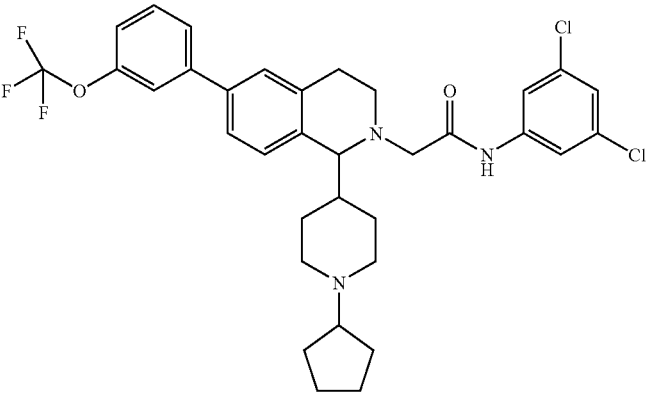 | $C_{34}H_{36}Cl_2F_3N_3O_2$ | 646.586 | 646.1 |
| 9 | 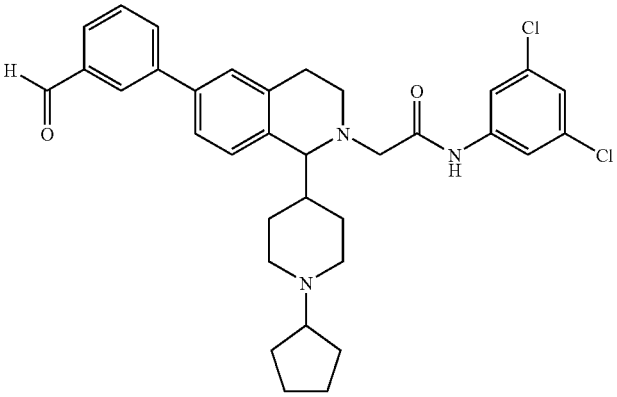 | $C_{34}H_{37}Cl_2N_3O_2$ | 590.599 | 590.1 |

TABLE 1-continued

Examples 1-45

| EX | MOLSTRUCTURE | MOL FORMULA | MOL WGT | Obsd m/z |
|----|--------------|-------------|---------|----------|
| 10 | | $C_{33}H_{35}Cl_4N_3O$ | 631.478 | 631.1 |
| 11 | | $C_{36}H_{38}Cl_2N_4O$ | 613.636 | 613.1 |
| 12 | | $C_{32}H_{36}Cl_2N_4O$ | 563.576 | 563.1 |

TABLE 1-continued

Examples 1-45

| EX | MOLSTRUCTURE | MOL FORMULA | MOL WGT | Obsd m/z |
|---|---|---|---|---|
| 13 | | $C_{31}H_{35}Cl_2N_3OS$ | 568.614 | 568.1 |
| 14 | | $C_{36}H_{39}Cl_2N_5O$ | 628.651 | 628.1 |
| 15 | | $C_{31}H_{36}Cl_2N_4O$ | 551.565 | 551.1 |

TABLE 1-continued

Examples 1-45

| EX | MOLSTRUCTURE | MOL FORMULA | MOL WGT | Obsd m/z |
|----|--------------|-------------|---------|----------|
| 16 | | $C_{32}H_{36}Cl_2N_4O$ | 563.576 | 563.1 |
| 17 | | $C_{30}H_{30}Cl_2N_4O$ | 533.506 | 533.1 |
| 18 | | $C_{34}H_{37}Cl_2N_3O_3$ | 606.598 | 606.1 |

TABLE 1-continued
Examples 1-45
| EX | MOLSTRUCTURE | MOL FORMULA | MOL WGT | Obsd m/z |
|----|--------------|-------------|---------|----------|
| 19 | 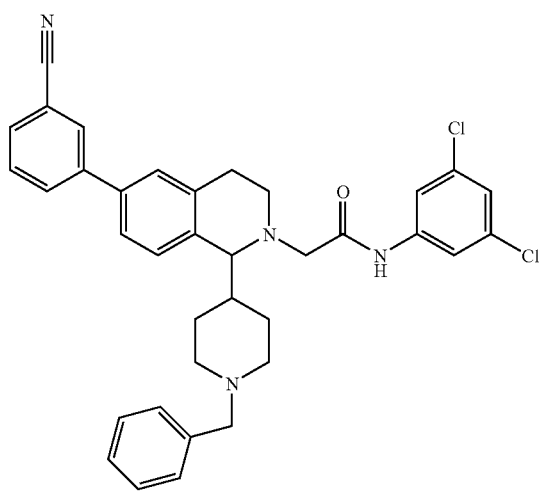 | $C_{36}H_{34}Cl_2N_4O$ | 609.605 | 609.1 |
| 20 | 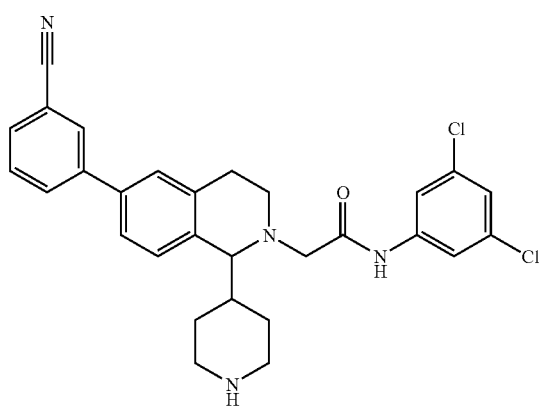 | $C_{29}H_{28}Cl_2N_4O$ | 519.479 | 519.1 |
| 21 | 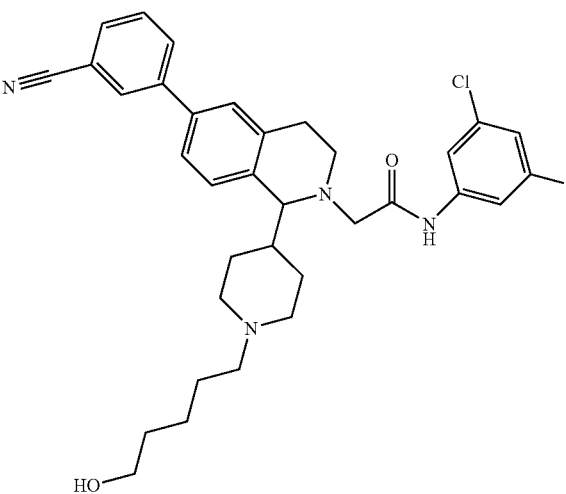 | $C_{34}H_{38}Cl_2N_4O_2$ | 605.614 | 605.1 |

TABLE 1-continued

Examples 1-45

| EX | MOLSTRUCTURE | MOL FORMULA | MOL WGT | Obsd m/z |
|----|--------------|-------------|---------|----------|
| 22 | | $C_{36}H_{40}Cl_2N_4O$ | 615.652 | 615.1 |
| 23 | | $C_{35}H_{39}Cl_2N_5O$ | 616.64 | 616.1 |
| 24 | | $C_{34}H_{36}Cl_2N_4O_2$ | 603.589 | 603.1 |

TABLE 1-continued
Examples 1-45
| EX | MOLSTRUCTURE | MOL FORMULA | MOL WGT | Obsd m/z |
|---|---|---|---|---|
| 25 | 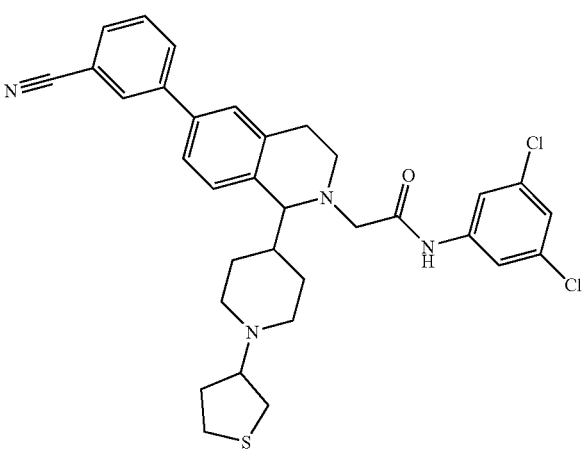 | $C_{33}H_{34}Cl_2N_4OS$ | 605.635 | 605.1 |
| 26 | 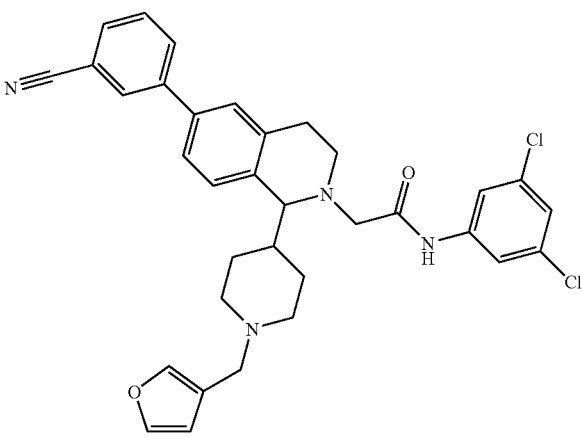 | $C_{34}H_{32}Cl_2N_4O_2$ | 599.566 | 599.1 |
| 27 | 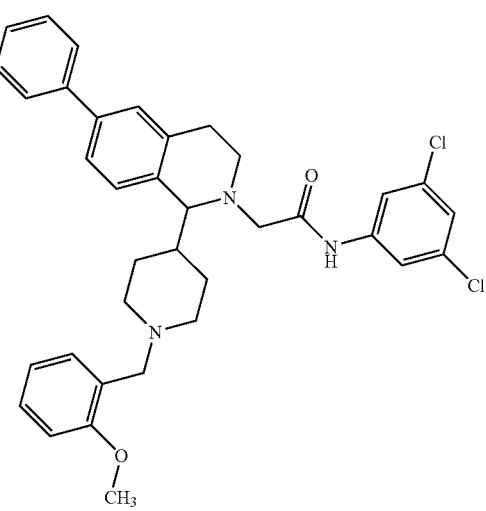 | $C_{37}H_{36}Cl_2N_4O_2$ | 639.631 | 639.2 |

TABLE 1-continued

Examples 1-45

| EX | MOLSTRUCTURE | MOL FORMULA | MOL WGT | Obsd m/z |
|---|---|---|---|---|
| 28 | | $C_{33}H_{34}Cl_2N_4O$ | 573.571 | 573.1 |
| 29 | | $C_{33}H_{34}Cl_2N_4O$ | 573.571 | 573.1 |
| 30 | | $C_{38}H_{38}Cl_2N_4O$ | 637.659 | 637.2 |

TABLE 1-continued

Examples 1-45

| EX | MOLSTRUCTURE | MOL FORMULA | MOL WGT | Obsd m/z |
|----|--------------|-------------|---------|----------|
| 31 | | $C_{32}H_{34}Cl_2N_4O$ | 561.56 | 561.1 |
| 32 | | $C_{35}H_{38}Cl_2N_4O$ | 601.625 | 601.1 |
| 33 | | $C_{35}H_{36}Cl_2N_4O_2$ | 615.609 | 615.1 |

TABLE 1-continued

Examples 1-45

| EX | MOLSTRUCTURE | MOL FORMULA | MOL WGT | Obsd m/z |
|---|---|---|---|---|
| 34 | | $C_{34}H_{37}Cl_2N_5O_2$ | 618.612 | 618.1 |
| 35 | | $C_{31}H_{30}Cl_2N_4O$ | 561.516 | 561.1 |
| 36 | | $C_{30}H_{30}Cl_2N_4O_3S$ | 597.569 | 597.1 |

TABLE 1-continued

Examples 1-45

| EX | MOLSTRUCTURE | MOL FORMULA | MOL WGT | Obsd m/z |
|---|---|---|---|---|
| 37 | | $C_{31}H_{33}Cl_2N_5O_3S$ | 626.61 | 626.1 |
| 38 | | $C_{33}H_{31}Cl_2N_5OS$ | 616.618 | 616.1 |
| 39 | | $C_{31}H_{32}Cl_2N_4O_3S$ | 611.596 | 611.1 |

TABLE 1-continued

Examples 1-45

| EX | MOLSTRUCTURE | MOL FORMULA | MOL WGT | Obsd m/z |
|----|---|---|---|---|
| 40 | | $C_{35}H_{32}Cl_2N_4O$ | 595.578 | 595.1 |
| 41 | | $C_{35}H_{32}Cl_2N_4O$ | 595.578 | 595.1 |
| 42 | | $C_{36}H_{35}N_5$ | 537.70 | 538.1 |

TABLE 1-continued
Examples 1-45
| EX | MOLSTRUCTURE | MOL FORMULA | MOL WGT | Obsd m/z |
|----|--------------|-------------|---------|----------|
| 43 | 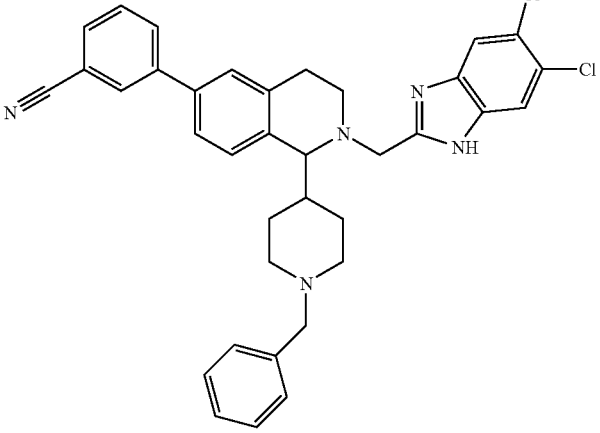 | $C_{36}H_{33}Cl_2N_5$ | 606.59 | 606.1 |
| 44 | 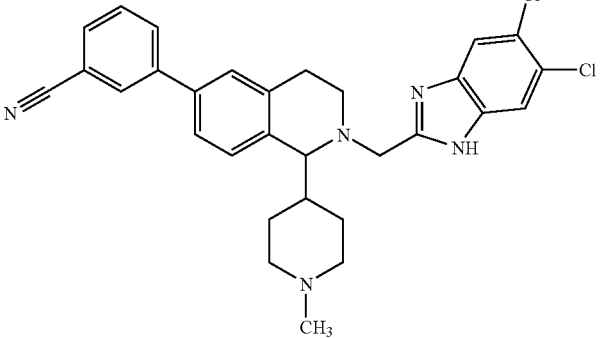 | $C_{30}H_{29}Cl_2N_5$ | 530.49 | 530.1 |
| 45 | 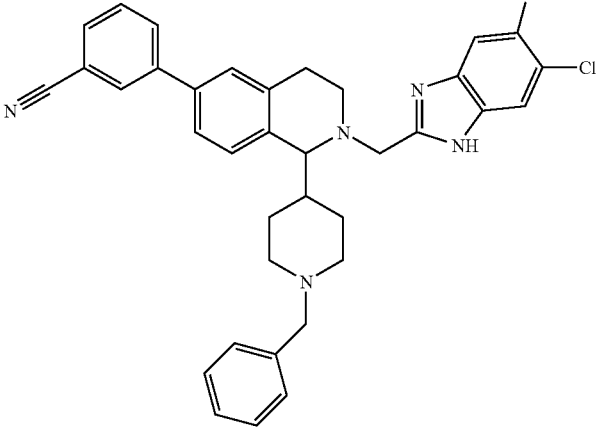 | $C_{36}H_{33}ClFN_5$ | 590.13 | 590.3 |

The compounds of Formula 1 exhibit MCH receptor antagonizing activity, which been correlated with pharmaceutical activity for treating disorders such as obesity hyperphagia, and diabetes, as well as eating disorders generally.

The compounds of Examples 1-45 (structures shown in Table 1) were tested for MCH receptor antagonizing activity as described above. Dissociation constants for particularly preferred compounds appear in Table 2. Results for other compounds appear in Table 3 where the compounds are rated "A" for Ki values of from 1 nM to 100 nM, "B" for Ki values of from greater than 100 nM to less than 500 nM and "C" for Ki values greater than 500 nM.

TABLE 2

MCH Receptor Activity
(Preferred Compounds)

| Example No. | MOLSTRUCTURE | Ave KiMCH |
|---|---|---|
| 1 | | 11.2 |
| 12 | | 24 |
| 16 | | 23 |

TABLE 2-continued

MCH Receptor Activity
(Preferred Compounds)

| Example No. | MOLSTRUCTURE | Ave KiMCH |
|---|---|---|
| 17 | *structure* | 22 |
| 19 | *structure* | 23 |
| 20 | *structure* | 26 |

TABLE 2-continued

MCH Receptor Activity
(Preferred Compounds)

| Example No. | MOLSTRUCTURE | Ave KiMCH |
|---|---|---|
| 21 | | 6.8 |
| 22 | | 10 |
| 24 | | 6.4 |

TABLE 2-continued

MCH Receptor Activity
(Preferred Compounds)

| Example No. | MOLSTRUCTURE | Ave KiMCH |
|---|---|---|
| 25 | | 7 |
| 26 | | 14 |
| 27 | | 16 |

TABLE 2-continued

MCH Receptor Activity (Preferred Compounds)

| Example No. | MOLSTRUCTURE | Ave KiMCH |
|---|---|---|
| 28 | (structure) | 9.3 |
| 29 | (structure) | 15 |
| 32 | (structure) | 10 |

TABLE 3

MCH Receptor Antagonist Activity

| Compound of Example | Av. MCH Ki |
|---|---|
| 2 | B |
| 3 | B |
| 4 | A |

TABLE 3-continued

MCH Receptor Antagonist Activity

| Compound of Example | Av. MCH Ki |
|---|---|
| 5 | A |
| 6 | A |
| 7 | B |

TABLE 3-continued

MCH Receptor Antagonist Activity

| Compound of Example | Av. MCH Ki |
|---|---|
| 8 | A |
| 9 | A |
| 10 | A |
| 11 | C |
| 13 | B |
| 14 | A |
| 15 | B |
| 18 | C |
| 19 | A |
| 23 | A |
| 30 | A |
| 31 | A |
| 33 | C |
| 34 | B |
| 35 | C |
| 36 | C |
| 37 | B |
| 38 | B |
| 39 | C |
| 40 | C |
| 41 | C |
| 42 | B |
| 43 | A |
| 44 | B |
| 45 | A |

What is claimed is:

1. A compound represented by the structural formula:

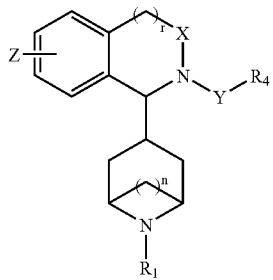

Formula 1 or a pharmaceutically acceptable salt of said compound, stereoisomer or racemate wherein X is —$CH_2$—, carbonyl, —$CHCH_3$ or —$C(CH_3)_2$—;

Y is —$(CR_2R_3)_p$—, —$(CR_2R_3)_pC(O)NH$—, —$(CR_2R_3)_p NH$—, —$C(O)NH$—, —$C(O)(CR_2R_3)_pNH$—, —$C(O)C(O)NH$— or —$C(O)(CR_2R_3)_p$—;

Z is phenyl, 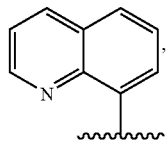, 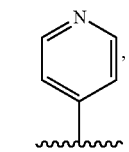,

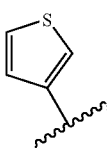, 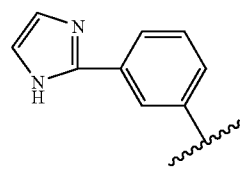, or

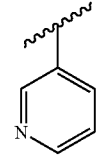, wherein any of the foregoing radicals for Z may be unsubstituted or optionally independently substituted with a cyano, fluoro, chloro, methoxy, trifluoromethyl, trifluoromethoxy, formyl or a carboxyl group, or alternatively Z is a 2,5-dichlorophenyl;

n is 0, and when n is 0, no connecting bond exists between the two carbons adjacent to the nitrogen;

p is 1, 2 or 3;

r is 1;

$R_1$ is hydrogen, cyclopentyl, methyl, benzyl, 5-hydroxy-n-pentyl, cycloheptyl, N-methylpiperidine-4-yl, 4-oxacyclohexyl, 3-thiacyclopentyl, furane-3-ylmethyl, 2-methoxybenzyl, cyclopropylmethyl, cyclobutyl, 3-phenylpropyl, isopropyl, cyclohexyl, cyclopentylcarbonyl, diethylaminocarbonyl, acetyl, methylsulfonyl, dimethylaminosulfonyl, thiazole-2-ylmethyl, or ethylsulfonyl;

$R_2$ and $R_3$ can be the same or different, each being independently hydrogen, or alkyl; and $R_4$ is phenyl substituted with halogen or

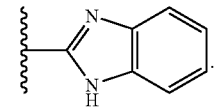.

2. A compound according to claim 1 wherein X is —$CH_2$, —$CHCH_3$ or —$C(CH_3)_2$—.

3. A compound according to claim 1 wherein Y is —$(CR_2R_3)_pC(O)NH$—, —$C(O)NH$—, —$C(O)(CR_2R_3)_p NH$— or —$C(O)C(O)NH$—.

4. A compound according to claim 1 wherein p is 1.

5. The compound of claim 1, wherein Z is cyanophenyl or pyridinyl.

6. The compound of claim 5, wherein Z is cyano-3-phenyl.

7. The compound of claim 5, wherein Z is pyridine-3-yl.

8. The compound of claim 5, wherein Z is pyridine-4-yl.

9. The compound of claim 1, wherein $R_4$ is 3,5-dichlorophenyl.

10. The compound of claim 1, wherein $R_1$ is methyl.

11. The compound of claim 1, wherein Y is —$C(R_2R_3)C(O)NH$—.

12. The compound of claim 1 wherein and $R_2$ and $R_3$ are hydrogen.

13. The compound of claim 1 wherein:

X is carbonyl;

Y is —$C(R_2R_3)C(O)NH$—; and $R_2$ and $R_3$ are hydrogen, or alkyl.

14. The compound of claim 13 wherein $R_2$ and $R_3$ are hydrogen.

15. The compound of claim 1 wherein X is —$CH_2$—.

16. The compound of claim 1, wherein $R_1$ is hydrogen;

$R_2$ and $R_3$ are hydrogen, or alkyl;

n is 0;

r is 1; and

Z is phenyl.

17. A compound, or a pharmaceutically acceptable salt of said compound, stereoisomer or racemate, wherein said compound is selected from the group consisting of:
Ex. 1
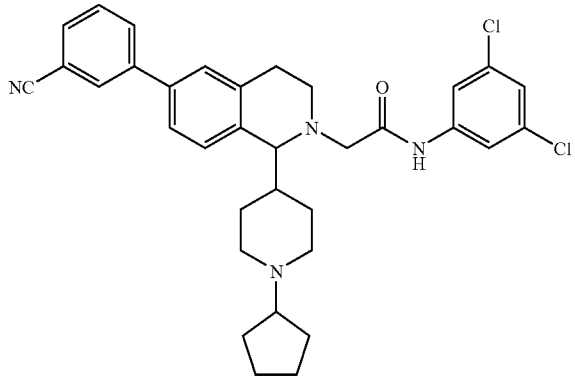
Ex. 12
Ex. 16
-continued
Ex. 17
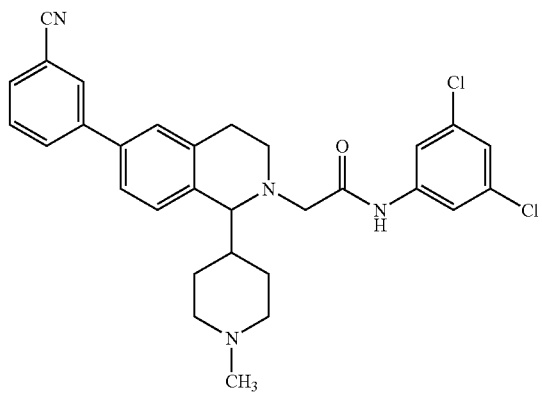
Ex. 19
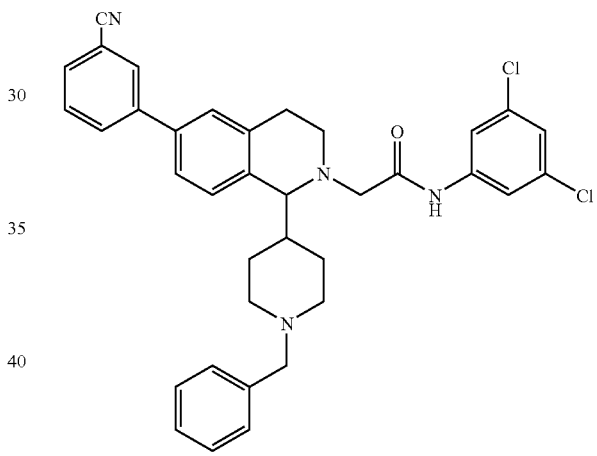
Ex. 20
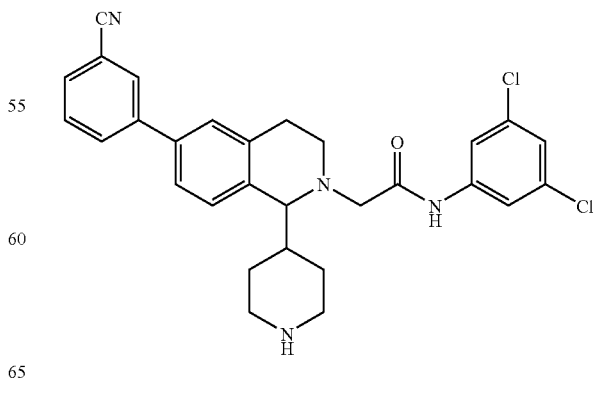

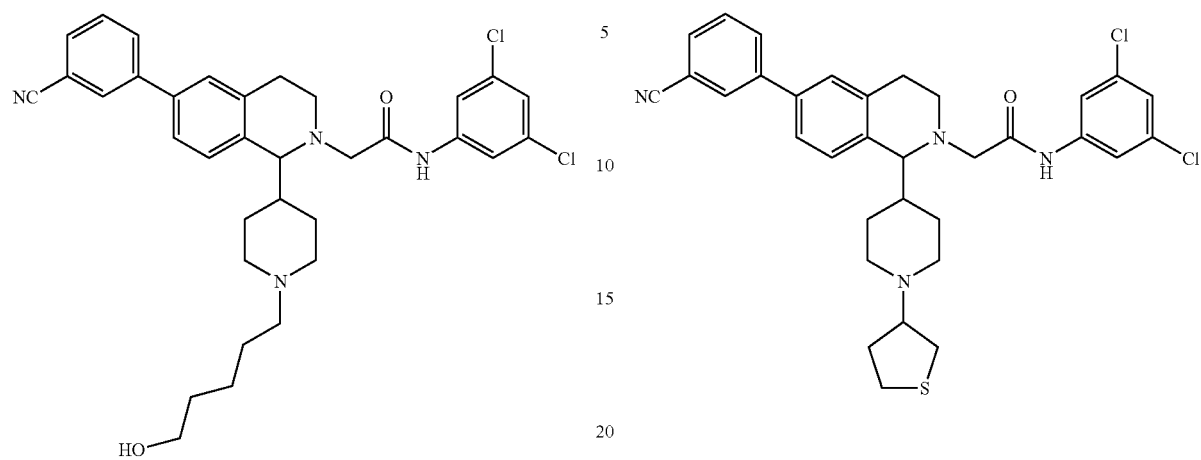
Ex. 21
Ex. 25
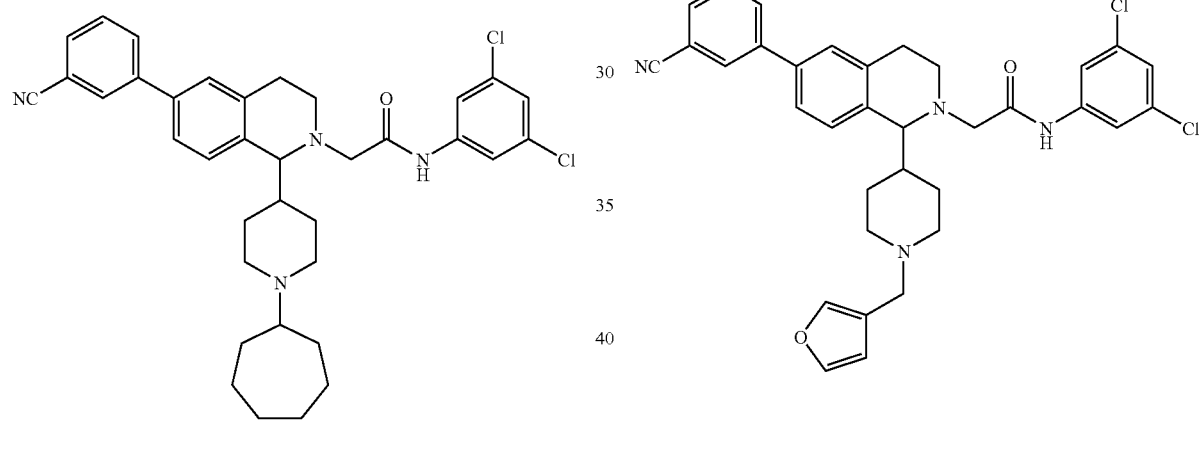
Ex. 22
Ex. 26
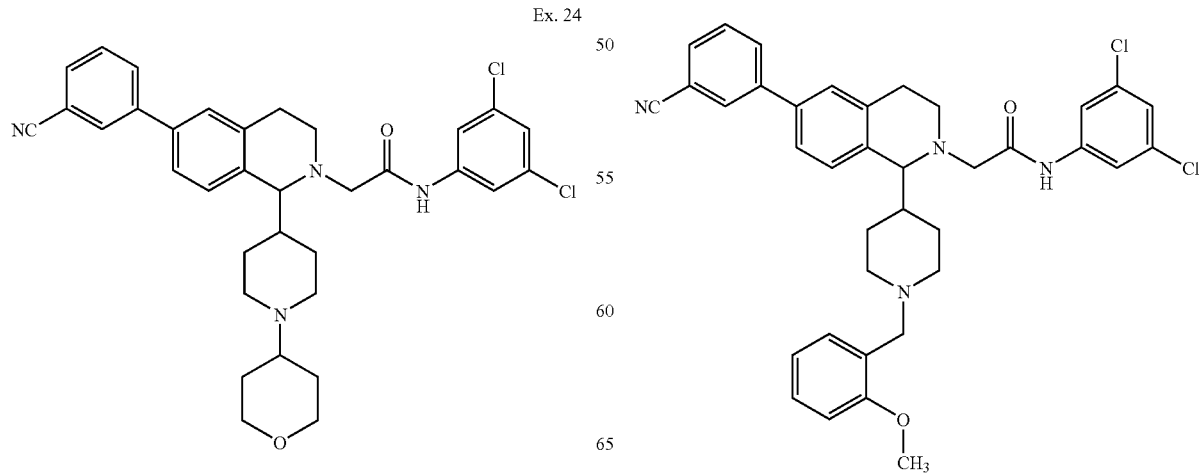
Ex. 24
Ex. 27

-continued

Ex. 28
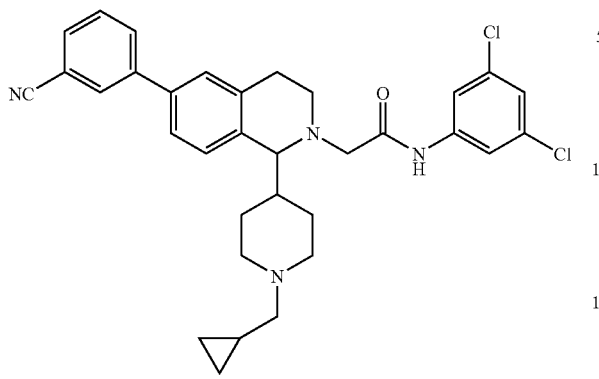

Ex. 29

Ex. 32
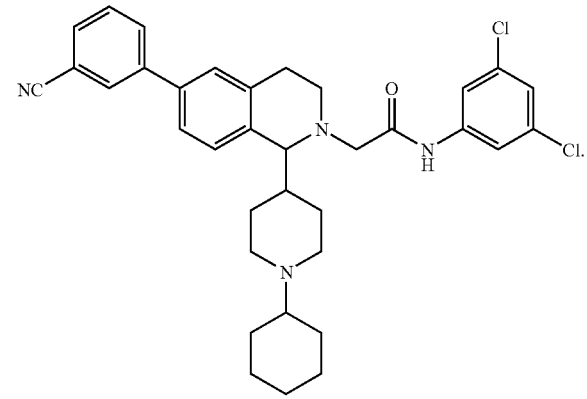

and

18. A pharmaceutical composition comprising a therapeutically effective amount of at least one compound of claim 1 in combination with at least one pharmaceutically acceptable carrier.

19. A pharmaceutical composition comprising a therapeutically effective amount of at least one compound of claim 17 in combination with at least one pharmaceutically acceptable carrier.

* * * * *